United States Patent [19]
Brockman et al.

[11] 4,089,589
[45] May 16, 1978

[54] OPTICAL SIGNAL PROCESSING SYSTEM AND METHOD

[75] Inventors: William Harry Brockman, Ames, Iowa; Robert Frank Cannata, Torrance, Calif.

[73] Assignee: Iowa State University Research Foundation, Inc., Ames, Iowa

[21] Appl. No.: 685,270

[22] Filed: May 11, 1976

[51] Int. Cl.$^2$ .............................................. G02B 5/18
[52] U.S. Cl. .............................. 350/162 SF; 235/181
[58] Field of Search ................... 350/162 SF; 235/181

[56] References Cited

U.S. PATENT DOCUMENTS

| | | | |
|---|---|---|---|
| 2,787,188 | 4/1957 | Berger | 235/181 X |
| 3,492,469 | 1/1970 | Silverman | 350/162 SF |

OTHER PUBLICATIONS

L. J. Cutrona et al., "Optical Data Processing and Filtering Systems," IRE Trans. on Information Theory, June 1960, pp. 386–400.
A. Vander Lugt, "Signal Detection by Complex Spatial Filtering," IEEE Trans. on Information Theory, Apr. 1964, pp. 139–145.
G. W. Stroke, Introduction to Coherent Optics and Holography, Academic Press, New York, 1969, pp. 79–86.
S. H. Lee, "Mathematical Operations by Optical Processing," Optical Engineering, vol. 13, No. 3, May/June 1974, pp. 196–207.

*Primary Examiner*—John K. Corbin
*Assistant Examiner*—John D. Lee
*Attorney, Agent, or Firm*—Tilton, Fallon, Lungmus & Chestnut

[57] ABSTRACT

The optical system includes a point source of monochromatic light which is focused by a first lens onto a frequency plane. A pair of transparencies bearing information in a single-axis density-modulated form are interposed before the frequency plane. The transparencies may be arranged so that the information axis of one is angularly displaced 90° relative to the information axis of the other. A slit is placed at the frequency plane at a 45° angle relative to the axes of the transparencies so that the only light transmitted beyond the frequency plane is that which is passed through the slit. The light passing through the slit is focused by a second lens onto an image plane; and the resulting output image (read parallel to the direction of elongation of the slit) is the mathematical convolution or correlation function of the input signals, depending on whether the slit is placed at a +45° angle or a −45° angle. The output image may be read electronically or stored photographically or otherwise.

15 Claims, 13 Drawing Figures

$$\frac{1}{d_3} + \frac{1}{d_4} = \frac{1}{F}$$

$$\frac{1}{d_1} + \frac{1}{d_2} = \frac{1}{F}$$

Fig. 12

OPTICAL SIGNAL PROCESSING SYSTEM AND METHOD

BACKGROUND AND SUMMARY

The present invention relates to an optical signal processing system and method; and more particularly, it relates to an optical signal processor wherein two separate optical images are combined in such a manner that the output optical image is a predetermined mathematical function of the information contained in the separated input images.

The inherent two-dimensional parallel processing capabilities of coherent optical systems have led to many diverse applications of optical processing. A vast majority of these applications have been concerned with spatial frequency processing of two-dimensional data such as photographs. The development, by Vander Lugt, of a holographic technique to produce complex spatial filters has enabled the mathematical operations of convolution and correlation to be applied in the analysis of two-dimensional data. The implementation of these filters has further diversified the applications of optical processing. However, the application of these optical techniques to the analysis of one-dimensional data has been quite limited even though many of the advantageous properties of optical computation are also applicable to the processing of such data. The present invention, thus, is directed to an optical system which will enable instantaneous and simultaneous spectral analysis of two signal records or images; and, with the use of a simple narrow slit spatial filter in the frequency plane, the operations of convolution and correlation of the two signal images can be obtained without the need to holographically record the frequency spectrum of one signal record prior to processing.

The present invention has utility in the comparison of one optical image with a second optical image, and it could be used, for example, as a medical diagnostic system. In this case, again as an example, one of the input images would bear information representative of a reference electrocardiogram (ECG) or an earlier ECG of the same patient. The second optical image could be a more recent ECG of the patient. Simply by placing the two optical images in the present system, there is immediately produced a correlation or convolution of the two input images; and the output is immediately present in optical form so that it is easily read electronically or stored on film, for example.

For an electronic system to be capable of performing similar computational functions, such as correlations or convolutions, of two independent input signals as complex as ECGs, the system would have to require a substantial amount of costly hardware such as analog-to-digital converters, and also possess substantial computational capacity. Even then, it would take some time for the output results to be generated.

In the present invention, the input information is stored on optical transparencies in a "density-modulated" form. As used herein, a "density-modulated transparency" is one in which the density of the image bearing the information is modulated such that the light amplitude transmission of the transparency is proportional to the amplitude of the signal to be processed. The intensity of light is proportional to the square of the amplitude, and whereas physical systems deal with light intensity rather than light amplitude, this distinction should be borne in mind throughout. The transparencies bearing the input information are density-modulated only in one direction, called the "information" axis. For example, the density of the image may vary left-to-right, but will remain constant along all vertical lines. Methods of recording information on transparent film by density modulation are known in the art, and some of these methods are discussed below. In summary, the information to be processed is recorded on an optical transparency as a spatial light amplitude variation along the information axis.

The mathematical and physical principles of optical computing are based primarily on the phenomenon of diffracted monochromatic light and the inherent optical properties of a thin converging lens. The information to be processed by this technique is recorded on an optical transparency as a spatial light amplitude variation. Illuminating this transparency with monochromatic light results in diffraction of the light in a manner determined by the amplitude and phase at each point on the back side of the transparency. The function of the thin converging lens is to focus the diffraction pattern on an appropriate plane behind the lens. The resultant amplitude and phase of the light distribution across this plane is directly proportional to the two-dimensional Fourier transform of the light amplitude transmitted by the input transparency—thus this plane is sometimes referred to as the frequency plane.

An optically produced one-dimensional Fourier transform is a special case of this two-dimensional transformation. Optical processing of one-dimensional data, such as biological signals, requires an initial conversion of the signal into the spatial domain. This may be accomplished by properly recording the signal on an optical transparency such that the light amplitude transmittance as a function of one spatial coordinate is directly related to the input signal amplitude as a function of time. Illuminating this transparency with coherent light will produce an optical Fourier transform pattern behind the converging lens. The light amplitude distribution along one spatial coordinate in the transform plane will be directly related to the one-dimensional Fourier transform of the input signal.

According to the present invention, then, a point source of monochromatic light is focused by a thin converging lens onto the frequency plane. Between the source and the frequency plane, two one-dimensional density-modulated transparencies are placed together in the light path. The tranparencies extend perpendicular to the light path. One transparency may contain reference data. The other transparency may contain the "input" information desired to be processed or compared. The two transparencies are oriented relative to each other such that their information axes define a predetermined angle. In other words, the density-modulated information on each transparency is one-dimensional in the sense that the information is contained only along the information axis. When the two transparencies are juxtaposed, the information axes are placed at a 90° angle.

By placing the two transparencies as just described, the product of the Fourier transforms of the two independent input signals will appear along a line in the frequency plane. This line, if taken along the +45° axis will contain information representative of the product of the two transforms; and if taken along the −45° axis, it will also be the product of the two transforms. However, the argument of frequency in one of the functions will be minus in the latter case.

Thus, a slit is arranged in the frequency plane, for this example, at an angle of plus or minus 45° depending upon whether a convolution or correlation function is desired. The only information that passes through the slit, therefore, is the product of the two transforms at an angle of the slit. Thereafter, an inverse transform is performed by a thin converging lens onto an image plane. In optics, a second transformation is the same as an inverse transformation, as explained above.

Thus, the second converging lens produces an image of the input transparencies at the output or image plane, performing a Fourier transform from the frequency plane to the image plane, which transform is an inverse Fourier transform mathematically.

Output information is obtained by scanning the image plane in a direction parallel to the direction of elongation of a slit in the frequency plane. The result is a measurement of light intensity which is the square of the convolution or correlation function (again, because a physical system deals with intensity, not light amplitude).

An alternative embodiment is also disclosed wherein only a single converging lens is used to obtain the same results. It will be appreciated by persons skilled in the art that the light source need only be a point source of monochromatic light of fairly large intensity—it need not necessarily be coherent light.

Other features and advantages of the present invention will be apparent to persons skilled in the art from the followng detailed description of various embodiments, accompanied by the attached drawing wherein identical reference numerals will refer to like parts in the various views.

DETAILED DESCRIPTION

I. Preparing Density-Modulated Transparency

One method of recording a one-dimensional signal on a transparency is to use the signal to density modulate photographic film.

This technique utilizes the density exposure characteristics of photographic film, and thus some fundamental properties of photographic film must be considered.

Unexposed film consists of a light sensitive emulsion on a base support consisting typically of acetate. The photosensitive material is a mixture of very small silver halide crystals suspended in gelatin. The size of the crystals is approximately one micron, and as a general rule the larger the silver halide crystals the greater a film's sensitivity to light. It is an empirical observation that regardless of size, a silver halide crystal requires a certain number of absorbed photons to excite it. Thus, films with large crystals require fewer photons to achieve a specified density level than films containing smaller crystals. However, a film with large crystals will lack the capability of recording fine details. A film containing smaller crystals has greater resolution capabilities, but it is less sensitive to light and thus requires a longer exposure time to absorb the needed number of photons.

When the photosensitive emulsion is exposed to light, the silver halide crystals absorb photons and undergo a complex physical change. This physical change is not usually visible until the film is subject to the action of a developer. The developer chemically changes the exposed silver halide crystals into metallic silver grains. The unexposed crystals are not affected by the action of the developer and can be removed by a chemical fixing solution. Since the silver grains are nearly opaque and the film base is essentially clear the opacity of the developed film will depend upon the density of silver grains in each region of the film. The light intensity transmittance of the develped film transparency is defined as $$\tau_f(x,y) = I_T/I_o \quad (1)$$

where $I_T$ is the light intensity transmitted at $(x,y)$ and $I_o$ the incident light intensity at $(x,y)$. The film density is defined as $$D = \log \frac{I_o}{I_T} = \log \left(\frac{1}{\tau_f}\right) \quad (2)$$

A photographic emulsion that is exposed to a constant light intensity will have a developed image whose density (within limits) will increase with increasing exposure time. The relationship between density and exposure is represented by a graph called the characteristic curve. The graph is obtained by plotting the density versus the common logarithm of exposure. Film exposure is defined as $$E = I_s t \quad (3)$$

where $I_s$ is incident intensity of the light exposing the film, and $t$ is the exposure time.

When the exposure is below a certain level, the density is independent of the exposure and is equal to a minimum value called the fog level. As the exposure is increased from this point, the density increases non-linearly toward a region where it then increases linearly with the logarithm of exposure. The slope of the characteristic curve in this linear region is referred to herein as the film gamma ($\gamma$). It is in this linear region that photographic film is used for most conventional applications. Beyond the linear region, the density will increase only slightly with increasing exposure.

The shape of the characteristic for a photographic film will depend upon the nature of the emulsion and the method by which it was developed. A high contrast film is characterized by a large gamma, and a low contrast film has a low gamma. The value of gamma for each of these general film types is in turn affected by the developing process. The type of developing solution used, the temperature of this developer, and the developing time all have an effect on the value of gamma. In general, gamma will increase (within limits) as the time of developing or the developer temperature is increased. Thus, to completely describe the properties of a particular film, a family of characteristic curves is required.

Assuming that the film is used in the linear region of the characteristic curve, the density for a given developer, developing time and temperature is given by $$D = \gamma \log E + D_o = \gamma \log(I_s t) + D_o \quad (4)$$

where $D_o$ is a constant determined by the straight line approximation of the linear region. The incident intensity during exposure of the film can be related to the intensity transmittance after processing the film by equating Equations (2) and (4). The result may be written as $$\tau_I = K_1(I_s)^{-\gamma} \quad (5)$$

where $K_1$ is a constant.

Assuming that the film is of constant thickness, the amplitude and intensity transmittance are related by $$t(x,y) = [\tau_I(x,y)]^{\frac{1}{2}} = K_2(I_s)^{-\gamma/2} \quad (6)$$

It is further assumed that the incident light intensity is produced by a light source whose intensity is related to the input plus a constant bias by the following equation $$I_s = K_3/[B+g(t)]^c \quad (7)$$

where $K_3$, $c$, and $B$ are constants. If the light source is contained behind a narrow slit aperture and the film is moved at a constant speed past the aperture, then the amplitude transmittance of the developed film is $$t(x,y) = K_4[B+g(x)]^{\gamma c/2} \text{rect}(y/L_y) \quad (8)$$

where $K_4$ is a constant and $L_y$ is the width of the exposed film. Under the conditions that $\gamma c = 2$, a section of the film will have an amplitude transmittance given by $$t_o(x_o, y_o) = K_4[B+g(x_o)] \text{rect}(x_o/L_x) \text{rect}(y_o/L_y) \quad (9)$$

The two-dimensional Fourier transform of Equation (9) will reduce to $$T(f_x,f_y) = K_4BL_xL_y\,\text{sinc}(f_xL_x)\,\text{sinc}(f_yL_y) \quad (10)$$

$$+ K_4L_y\,\text{sinc}(f_y L_y) \int_{-\infty}^{\infty} g(x_o)\,\text{rect}(x_o/L_x)$$

$$\exp[-j2\pi f_x x_o]\,dx_o$$

and under the condition that $f_y = 0$, this transform further reduces to $$T(f_x,0) = K_4BL_y\,\text{sinc}(f_xL_x) \quad (11)$$

$$+ K_4L_y \int_{-\infty}^{\infty} g(x_o)\,\text{rect}(x_o/L_x)\,\exp[-j2\pi f_x x_o]\,dx_o$$

If $L_y$ is large, then Equation (10) is approximately $$T(fhd\ x,f_y) \simeq K_4BL_x\delta(f_y)\,\text{sinc}(f_xL_x) \quad (12)$$

$$+ K_4\delta(f_y) \int_{-\infty}^{\infty} g(x_o)\,\text{rect}(x_o/L_x)$$

$$\exp[-j2\pi f_x x_o]0\,dx_o$$

and the result will exist only along the $f_y = 0$ axis. Thus, a one-dimensional Fourier transform can be produced.

The function $\delta(f_y)$ is an impulse function defined as $$\delta(f_y) = \begin{cases} \infty & \text{for } f_y = 0 \\ 0 & \text{otherwise} \end{cases}$$

with the additional property that $$\int_{-\epsilon}^{\epsilon} \delta(f_y)df_y = 1 \quad (13)$$

for any $\epsilon > 0$.

It was assumed in the above development that the film thickness was constant. This assumption allowed the amplitude and intensity transmittance to be related by Equation (6). If the thickness is not constant, the optical path through the film is not constant and phase shifts will be introduced into the optical signal.

These undesirable phase shifts can be removed by placing the transparency between optically flat glass plates with an oil of matching index of refraction surrounding the film. The oil fills the voids between the optically flat glass and the film, thus making the transparency appear to be of constant thickness. This device is called a liquid gate.

Figure 1:
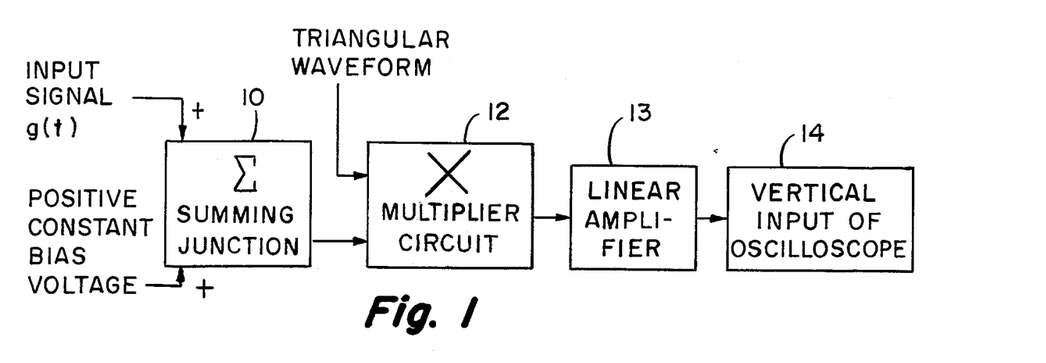
FIG. 1 is a functional block diagram of circuitry for intensity-modulating the beam of a cathode ray tube in a system for preparing intensity-modulated transparencies for use in the present invention.

A system to record a signal $g(t)$ on 35 mm, high contrast, black and white photographic film in a density modulated format is shown in FIG. 1. This system modulates the intensity of an oscilloscope by varying the writing rate of the oscilloscope beam. The function is to produce a beam with intensity characteristics inversely related to $g(t)$ raised to a power $c$. Referring to the previous discussion of density modulation, specifically the discussion leading to Equation (8), it is evident that processing the exposed film for the conditions that $\gamma c = 2$ will produce a transparency with amplitude transmittance characteristics directly related to the input signal as required for accurate optical computations.

Referring now to FIG. 1, the input signal $g(t)$ is assumed to be a low-frequency (below 60 Hz) signal with a maximum amplitude of 1.0 volt peak-to-peak. A positive constant bias voltage is added to $g(t)$ by feeding both signals to a summing circuit 10. The magnitude of the bias voltage is chosen to insure that output signal from the electronic summing circuit is positive even for negative values of $g(t)$. This permits recording the negative as well as the positive portions of $g(t)$. The output signal from the summing circuit is used to amplitude modulate a 4 volt peak-to-peak 5kHz triangular waveform by feeding both signals to a multiplier circuit 12. This modulated waveform was fed to a linear amplifier 13, the output of which is connected to the vertical input of an oscilloscope 14. The initial values for the constant bias voltage and the amplifier gain are set so that the minimum input waveform to the oscilloscope is 1.0 volt peak-to-peak.

The graticule on the oscilloscope is removed and the periphery of the cathode ray tube (CRT) is masked using opaque black tape to form a rectangular display area 9 cm long and 7 cm high. The vertical sensitivity of the oscilloscope is set at 0.1 volts/centimeter and the horizontal sweep rate is set at 0.33 seconds/centimeter. At this vertical sensitivity and sweep rate, a single vertical beam is linearly deflected across the CRT. The beam width is approximately 0.75 mm and the vertical displacement of the beam is directly related to the sum of the input signal $g(t)$ and the constant bias voltage. Since the CRT is masked in the vertical dimension, the vertical displacement appears to be constant and only the intensity appears to be varied as a function of $g(t)$ because of the changing beam writing rate. The beam writing rate increases as the amplitude of $g(t)$ increases and thus the intensity of the display decreases. Conversely, as $g(t)$ decreases, the beam writing rate also decreases and the intensity of the display increases. Thus, as the beam is linearly deflected across the CRT, the intensity at any instant along the vertical axis is constant and inversely related to $g(t)$ at that instant.

The intensity characteristics of the beam as a function of $g(t)$ may be expressed as $$I = K/[B+g(t)]^c \qquad (14)$$

where $K$, $B$, and the exponent $c$ are constants. This equation appears to be a good approximation to the physical system; and it also expresses the computational requirement of having a power relationship between the beam intensity and $g(t)$. It will be recalled that a power relationship is required so that the film processed for the conditions $\gamma c = 2$ produce a transparency with amplitude transmittance directly related to the signal of interest.

It was experimentally determined from horizontally static beam intensity measurements as a function of constant input signal voltages that the terms K, B, and c in Equation (14) are dependent upon the oscilloscope intensity level setting, the input bias voltage, and the amplifier gain. However, these static measurements are not an accurate representation of the dynamic horizontal sweep situation. The slight intensity halo around the oscilloscope beam and the phosphor decay time could not be included in these static measurements. Thus, the exact values for the terms K, B and c can not be predicted. The static measurements did, however, indicate the parameters controlling the exponent c. The magnitude of c is dependent upon the oscilloscope intensity level setting and the amplifier gain. In particular, c is directly related to the oscilloscope intensity level setting and inversely related to the gain of amplifier 13. This information, combined with a knowlege of the parameters controlling the film gamma, is used in a trial and error procedure to match the beam intensity characteristics of the particular CRT to the film processing. This procedure obviates the need to know the exact value of c and gamma in producing the desired result that $\gamma c = 2$.

The input bias voltage was set at 580 mv. A single lens reflex camera was attached to the oscilloscope at a distance of 45 cm from the CRT. The oscilloscope time base generator was equipped with a single sweep mode, thus permitting the camera shutter to be held open while a single linear sweep of the beam was recorded on film. With a relative lens aperture setting of $f/2.8$, single linear sweeps of the sinusoidal signal were recorded for one amplifier gain setting and various oscilloscope intensity level settings. The exposed film was then processed using the following procedure.

(1) The exposed film was developed in a high contrast developer (Kodak D-19 Developer, Eastman Kodak Company, Rochester, New York) for 8 minutes at 68° F, with agitation at 30 second intervals.

(2) The film was placed in a stop bath (Kodak Indicator Stop Bath, Eastman Kodak Company, Rochester, New York) solution for 30 seconds at 68° F. to neutralize the action of the developer.

(3) The film was placed in a fixer (Kodak Rapid Fixer with Hardener, Eastman Kodak Company, Rochester, New York) solution for 2 minutes at 68° F.

(4) The film was washed in water for 20 minutes at 68° F to remove residual chemicals remaining in the emulsion.

(5) The surface water was removed using a photographic squeegee, and the processed film was then dried by evaporation.

The film developing process was taken to completion by this technique and further increasing the developing time or the developer temperature had little effect on gamma. The value of gamma was at a maximum for this film ($\gamma = 3$).

The developed transparencies were then optically processed, and from the optically computed spectrum it was possible to measure the relative signal amplitude and the harmonic distortion in each transparency.

Figure 2A:
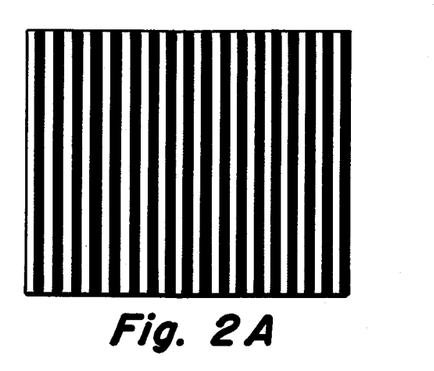
FIGS. 2A and 2B are photographic prints of density-modulated transparencies.
Figure 2B:
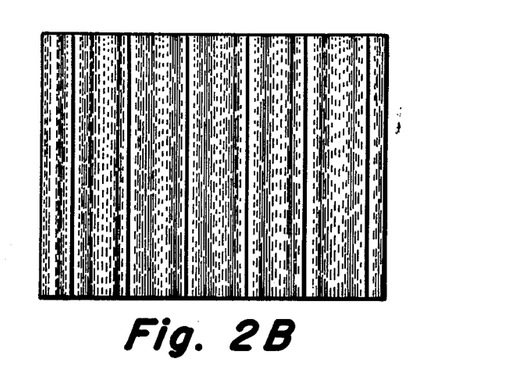

Photographic prints of two density modulated signal transparencies are shown in FIGS. 2A and 2B. A one centimeter length of these transparencies corresponded to two seconds. of real time data. In FIG. 2A, the input signal was a 1.0 volt peak-to-peak 10 Hz sinusoidal signal. FIG. 2B is a section of a canine ECG signal.

II. Optical System

Figure 3:
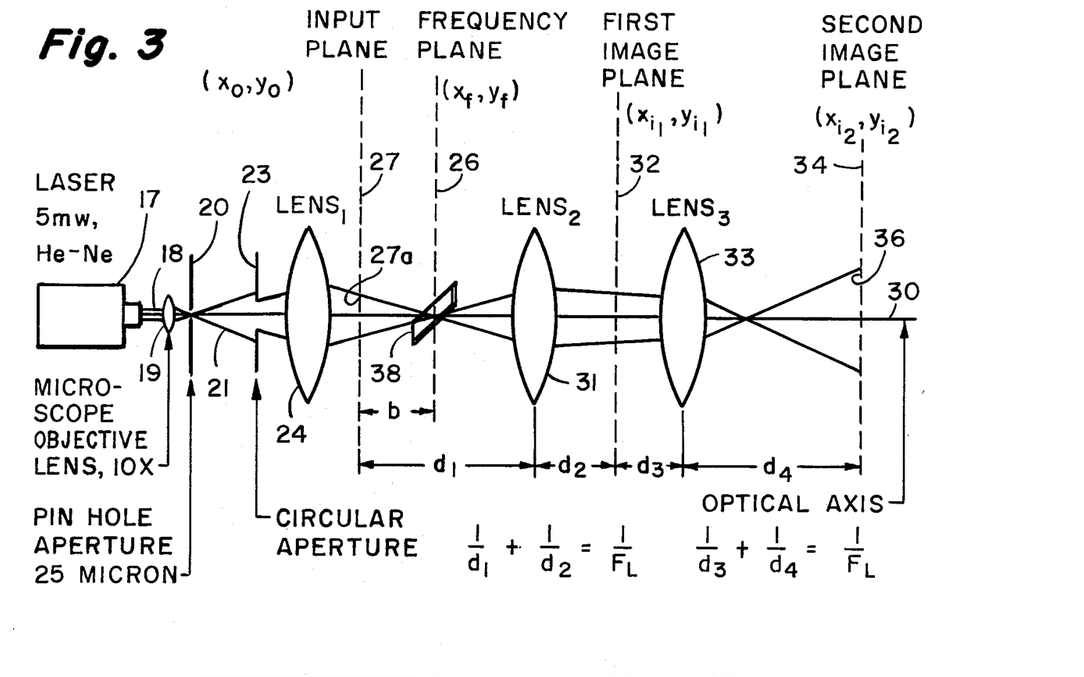
FIG. 3 is a diagrammatic illustration of an optical system to simultaneously process two separate density-modulated transparencies.

Referring now to FIG. 3, reference numeral 17 designates a continuous wave, single transverse mode heliumneon laser which generates a beam 18 of coherent monochromatic light. The beam 18 is focused by means of a microscope objective lens 19. Means 20 provide a pinhole aperture (two diameter sizes were used—10 micron and 25 micron), located at the point at which the beam converges. The function of the pinhole aperture is to spatially filter the converging beam to remove the undesirable off-axis spatial variations, as is commonly known. Thus, the light diverging from the pinhole is a good approximation of a uniform spherical wave diverging from a point source, as schematically illustrated by reference numeral 21.

A second means 23 provides another circular aperture (6mm. in diameter), and it is located between the pinhole and a converging lens 24. The aperture in the means 23 is used to limit the length in the signal transparency being processed, and to limit the illuminated lens area. By limiting the illuminated area to the central region of the lens 24, the paraxial aproximations for a thin lens become applicable. The lens 24 had a diameter of 52 mm., a focal length of 193 mm., and it was a coated, achromatic lens. The resulting beam is thus focused at a point lying in what is referred to as the frequency plane, diagrammatically illustrated by the line 26 which represents a plane extending perpendicular to the plane of the drawing. The transparencies to be processed are placed in the input plane 27, or as close to it as physically possible at a distance, b, from the frequency plane 26, and between the the lens 24 and the frequency plane 26. The position of the frequency plane may be determined by locating the image of the point source. This may be accomplished by placing a flat opaque object on the optical axis designated 30 in the neighborhood of the frequency plane and observing the reflected light distribution on a screen. This reflected light distribution is granular in appearance, and as the opaque object is moved along the optical axis 30, the granular size in the distribution varies. The exact location of the frequency plane is determined when a pattern with maximum granular size appears on the screen. This method utilizes the spatial coherence of the laser light source and the optical roughness of the reflecting surface.

A second lens 31 is used to focus the resulting beam toward a first image plane 32; and a third lens 33 focuses the image onto a second plane 34. The lens 33 is included merely to vary the size of the resulting images diagrammatically represented by the numeral 36.

Located at the frequency plane 26 is an opaque surface defining a slit 38 so that only light passing through the slit 38 is processed subsequent to the frequency plane 26.

III. Mathematical Development

Figure 4:
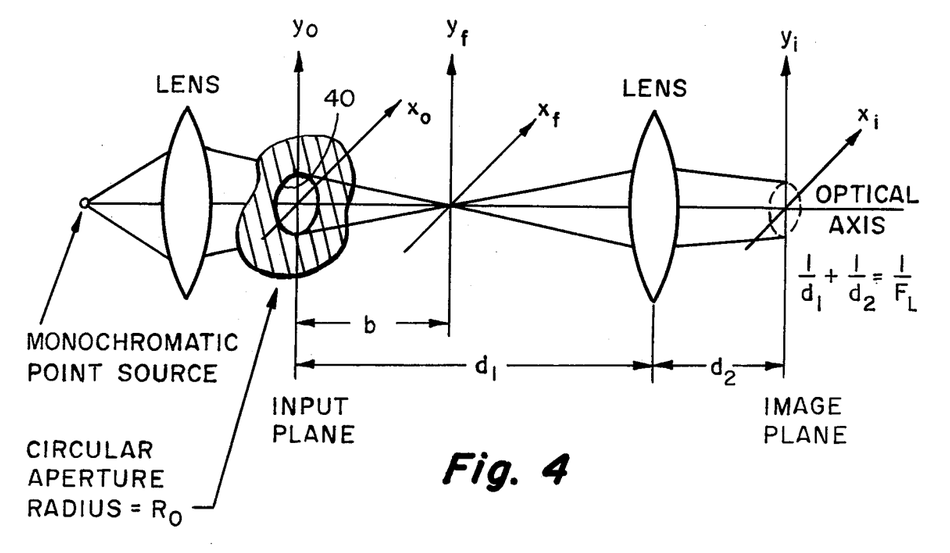
FIG. 4 is a diagrammatic illustration of an optical system to convolve and correlate two one-dimensional images recorded on transparencies in density-modulated format.

In this section, the two-dimensional Fourier transform properties of a coherent optical system is used to theoretically develop a technique to optically determine the convolution and the correlation functions for two one-dimensional signal records (i.e., density-modulated images recorded on transparencies). Referring now to FIG. 4, the circular aperture 40 which radius $R_o$ shown is used to limit the dimensions of the input plane.

In the following analysis, it will be assumed that two real one-dimensional signals $g_1(t)$ and $g_2(t)$ with zero average values are transcribed at the same sweep rate onto separate optical transparencies in the previously discussed density modulation format. Since only finite length sections of $g_1(t)$ and $g_2(t)$ can be transcribed onto film, in this development $g_1(t)$ and $g_2(t)$ may be time stationary random functions. The amplitude transmittance of the first transparency is $$t_1(x,y) = [B_1 + g_1(x)] \text{rect}(x/L_x) \text{rect}(y/L_y) \quad (15)$$

where $B_1$ is a positive constant bias term and the distances $L_x, L_y$ are, respectively, the length of the signal record in the x-direction and the width of the transparency in the y-direction. Similarly, the amplitude transmittance of the second transparency is $$t_2(x,y) = [B_2 + g_2(x)] \text{rect}(x/L_x) \text{rect}(y/L_y) \quad (16)$$

If the two transparencies are optically cascaded, then the amplitude transmittance of this combination will be $$t(x,y) = t_1(x,y)t_2(x,y) \quad (17)$$

However, if the second transparency is oriented along the positive y-axis such that the transmittance function $t_2(x,y)$ is now written as $t_2(y,x)$, then $t(x,y)$ is given by $$t(x,y) = t_1(x,y)t_2(y,x) \quad (18)$$

Since there is symmetry in the y-axis dimension of $t_2(x,y)$, thus $t_2(y,-x) = t_2(y,x)$.

Placing the cascaded transparencies in the input plane of the optical system of FIG. 4 causes the amplitude transmittance directly behind the input plane (when looking from the source) to be $$t_o(x_o,y_o) = t(x_o, y_o) \text{circ}(r_o/R_o) = t_1(x_o, y_o)t_2(y_o, x_o) \text{circ}(r_o/R_o) \quad (19)$$

where $\text{circ}(r_o/R_o)$ is a circular aperture function of radius $R_o$ defined as $$\text{circ}(r_o R_o) = \begin{cases} 1 \text{ for } r_o = [x_o^2 + y_o^2]^{\frac{1}{2}} \leq R_o \\ 0 \text{ otherwise} \end{cases} \quad (20)$$

If the radius $R_o$ is less than $L_x/2$ and $L_y/2$, then the transmittance function $t_o(x_o,y_o)$ is given by $$t_o(x_o, y_o) = [B_1 + g_1(x_o)][B_2 + g_2(y_o)] \text{circ}(r_o/R_o) \quad (21)$$

which is $$t_o(x_o,y_o) = [B_1B_2 + B_2g_1(x_o) + B_1g_2(y_o) + g_1(x_o)g_2(y_o)] \text{circ}(r_o/R_o) \quad (22)$$

The complex light amplitude distribution in the frequency plane is given by $$U_f(x_f,y_f) = K \exp\left[\frac{j\pi}{\lambda b}(x_f^2 + y_f^2)\right]\{t_o(x_0,y_0)\} \quad (23)$$

$$f_x = x_f/\lambda b, f_y = y_f/\lambda b$$

The Fourier transform of the circular aperture function is $$F\{\text{circ}(r_o/R_o)\} = R_o \frac{J_1[2\pi R_0(f_x^2 + f_y^2)^{\frac{1}{2}}]}{(f_{x2} + f_y^2)^{\frac{1}{2}}}$$

where $J_1$ is a Bessel function of the first kind, order one.

The two-dimensional impulse function $\delta(f_x,f_y)$ is defined as $$\delta(f_x,f_y) = \begin{cases} \phi \text{ for } f_x = f_y = 0 \\ 0 \text{ otherwise} \end{cases}$$

with the additional property that $$\int_\epsilon^\epsilon \delta(f_x,f_y)df_xdf_y = 1 \text{ for any } \epsilon_0 > 0.$$

Assuming that $R_o$ is large, the two-dimensional Fourier transform of the circular aperture function can be approximated by $$F\{\text{circ}(r_o/R_o)\} \simeq \delta(f_x,f_y) \quad (24)$$

where $\delta(f_x,f_y)$ is a two-dimensional impulse function.

The Fourier transform of $t_o(x_o,y_o)$ can then be approximated as $$F\{t_o(x_o,y_o)\} \approx [B_1B_2\delta(f_x,f_y) + B_2G_1(f_x)\delta(f_y) \\ + B_1G_2(f_y)\delta(f_x) + G_1(f_x)G_2(f_y)] * \delta(f_x,f_y) \\ = B_1B_2\delta(f_x,f_y) + B_2G_1(f_x)\delta(f_y) \\ + B_1G_2(f_y)\delta(f_x) + G_1(f_x)G_2(f_y) \quad (25)$$

The effect of the circular aperture function of the intensity distribution in the frequency plane is to produce a resolution limiting Airy pattern distribution around each discrete spectral point. The radius of the central maximum of the Airy pattern is $1.22 \lambda b/2R_o$.

Inasmuch as the complex light amplitude distribution in the frequency plane is directly related to $F\{t_o(x_o,y_o)\}$, it would be instructive at this point to consider the significance of each term in Equation 25. The first term represents the bias or zero frequency term that exists at the origin of the frequency plane. The second term is proportional to the frequency spectrum of $g_1(x_o)$ and exists along the $f_x$-axis ($x_f$-axis). Similarly, the third term is proportional to the frequency spectrum of $g_2(y_o)$ and exists along the $f_y$-axis ($y_f$-axis). The fourth term represents the distribution of off-axis terms which is dependent upon the product of the frequency spectrums of $g_1(x_o)$ and $g_2(y_o)$. Thus, the distribution in the frequency plane contains spectral information about each individual signal, and the product of the frequency spectrums for these signals.

Consider placing in the frequency plane a spatial filter with amplitude transmittance characteristics $$H\left(\frac{x_f}{\lambda b}, \frac{y_f}{\lambda b}\right).$$

The light amplitude distribution immediately behind the spatial filter is given by $$U_f(x_f, y_f) = K \exp\left[\frac{j\pi}{\lambda b}(x_f^2 + y_f^2)\right] \\ H\left(\frac{x_f}{\lambda b}, \frac{y_f}{\lambda b}\right) F\{t_o(x_o, y_o)\} \quad (26)$$

$$f_x = \frac{x_f}{\lambda b}, f_y = \frac{y_f}{\lambda b}$$

This is equivalent to having in the input plane an object transparency with amplitude transmittance characteristics $t'_o(x_o,y_o)$ such that $$F\{t'_o(x_o,y_o)\} = H(f_x,f_y) F\{t_o(x_o,y_o)\} \quad (27)$$

which can also be written as $$t'_o(x_o,y_o) = F^{-1}\{H(f_x,f_y) F\{t_o(x_o,y_o)\}\} \quad (28)$$

where $F^{-1}\{\}$ is the shorthand notation for the two-dimensional inverse Fourier transform. If $T_o(f_x,f_y)$ is the Fourier transform of $t'_o(x_o,y_o)$, then the inverse Fourier transform of $T'_o(f_x,f_y)$ written as $F^{-1}\{T'_o(f_x,f_y)\}$ is defined as $$F^{-1}\{T_o(f_x,f_y)\} = \int_{-\infty}^{\infty} T_o(f_x,f_y) \exp[j2\pi(f_xx_o + f_yy_o)] df_x df_y$$

$$= t'_o(x_o, y_o)$$

Thus, $t'_o(x_o, y_o)$ represents the spatially filtered version of the transmittance function $t_o(x_o, y_o)$. Then the distribution in the image plane is a spatially inverted magnified image of $t'_o$, and is given by $$U_i(x_i, y_i) = -\frac{d_1}{d_2} \exp\left[\frac{j2\pi}{\lambda}(d_1 + d_2)\right] \\ \exp\left[\frac{j\pi}{\lambda d_2}\left(1 + \frac{d_1}{d_2} - \frac{d_1^2}{bd_2}\right)(x_i^2 + y_i^2)\right] \\ t'_o\left(-\frac{d_1}{d_2}x_i, -\frac{d_1}{d_2}y_i\right) \quad (29)$$

providing that $H(f_x, f_y)$ does not produce any significant diffraction effects.

Figure 5:
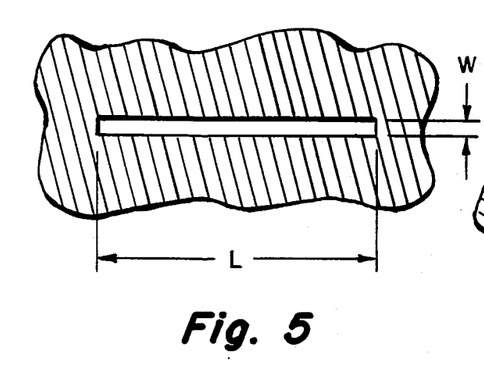
FIG. 5 is an illustration of a slit located at the frequency plane and extending horizontally.

If the spatial filter is a narrow rectangular aperture of length L and width W as shown in FIG. 5, and it is oriented symmetrically about the origin and along the $f_x$-axis ($x_f$-axis) in the frequency plane, then the amplitude transmittance of this filter can be written as $$H(f_x, f_y) = \text{rect}(f_x/L') \text{rect}(f_y/W') \quad (30)$$

where $$L' = L/\lambda b$$

and $$W' = W\lambda b$$

Thus, $t'_o(x_o, y_o)$ is given by $$t'_o(x_o, y_o) \quad (31) \\ = F^{-1}\left\{\text{rect}\left(\frac{f_x}{L'}\right)\text{rect}\left(\frac{f_y}{W'}\right) F\{t_o(x_o, y_o)\}\right\} \\ \approx F^{-1}\left\{\text{rect}\left(\frac{f_x}{L'}\right)\text{rect}\left(\frac{f_y}{W'}\right)[B_1B_2\delta(f_x, f_y) \\ + B_2G_1(f_x)\delta(f_y) + B_1G_2(f_y)\delta(f_x) \\ + G_1(f_x)G_2(f_y)]\right\}$$

Figure 6:
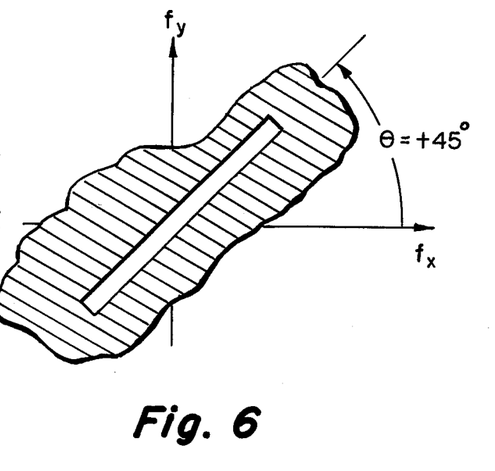
FIG. 6 is an illustration of the slit of FIG. 5 rotated in such a manner as to produce correlation of the input functions.

Consider now orienting the spatial filter symmetrically about the origin and at an angle $\theta$ from the positive $f_x$-axis as shown in FIG. 6. To reduce the complexity of the mathematical operations that follow, coordinate systems in the input, frequency, and image planes will be defined as follows:

$$x_0' = x_0 \cos\theta + y_0 \sin\theta$$

$$y_0' = -x_0 \sin\theta + y \cos\theta$$

$$f_x' = f_x \cos\theta + f_y \sin\theta$$

$$f_y' = -f_x \sin\theta + f_y \cos\theta$$

$$x_i' = x_i \cos\theta + x_i \sin\theta$$

$$y_i' = -x_i \sin\theta + y_i \cos\theta$$

The amplitude transmittance of the spatial filter is then given by $$H(f'_x, f'_y) = \text{rect}(f'_x/L') \text{rect}(f'_y/W') \quad (32)$$

and Equation (31) can be written as $$t_0'(x_0',y_0') = F^{-1}\{ \text{rect}(f_x/L') \text{rect}(f_y/W') F\{t_0(x_0,y_0)\}\} \quad (33)$$

$$\simeq F^{-1}\{\text{rect}(f_x/L')\text{rect}(f_y/W') [B_1B_2\delta(f_x,f_y)$$
$$+ B_2G_1(f_x)\delta(f_y) + B_1G_2(f_y)\delta(f_x)$$
$$+ G_1(f_x) G_2(f_y)]\}$$

where:

$$f_x = f_x' \cos\theta - f_y' \sin\theta$$
$$f_y = f_x' \sin\theta + f_y' \cos\theta \quad (34)$$

Assuming that $L'/2$ is large and $W'$ is small, then Equation (33) reduces to $$t_0'(x_0',y_0') \simeq F^{-1}\{\text{rect}(f_y/W') [B_1B_2\delta(f_x\cos\theta, f_x\sin\theta) \quad (35)$$
$$+ G_1(f_x\cos\theta)G_2(f_x\sin\theta)]\}$$

where assuming a small $W'$ (W approximating the diameter of the central maximum of the Airy pattern) eliminates the second and third terms in Equation (33) and the $f_y$ variable in Equation (34). Under these assumptions and by applying the scaling property of the Fourier transform, Equation (35) can be written as $$t_0'(x_0', y_0') \simeq \frac{1}{|\cos\theta||\sin\theta|}[B_1B_2 + \quad (36)$$
$$+ g_1(x_0'/\cos\theta) * G_2(x_0'/\sin\theta)]$$

If the angle Ⓗ is positive and equal to 45°, then the second term in Equation (36) is the convolution of $g_1(\sqrt{2} x_0')$ and $g_2(\sqrt{2} x_0')$. Thus, Equation (36) can be written as $$t_0'(x_0',y_0') \simeq 2[B_1B_2 + g_1(\sqrt{2} x_0') g_2[\sqrt{2} x_0')] \quad (37)$$

Considering just the one-dimensional relationship $t_0'(x_0',0)$, then the finite limits on the signal length can be reinserted into this result and $$t'(x',0) = 2[B_1B_2 + g_1(\sqrt{2} x_0') * g_2(\sqrt{2} x_0')]\text{rect}(x_0'/2R_0) \quad (38)$$

Thus, the light amplitude distribution along the $x_i'$-axis $(y_i' = 0)$ in the image plane is directly related to the convolution of $g_1$ and $g_2$ plus a constant term $B_1B_2$. This constant or zero frequency term can be optically filtered from the image distribution by placing a small opaque stop at the origin in the frequency plane. Therefore, the amplitude distribution in the image plane is directly related to the convolution of $g_1$ and $g_2$ spatially inverted (folded about the $x_i'$-axis) and magnified by a factor $d_2/d_1$.

Figure 7:
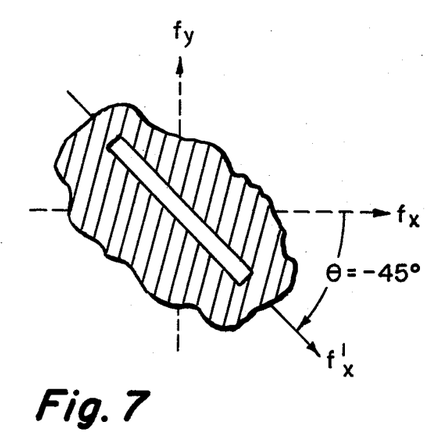
FIG. 7 is an illustration of the slit of FIG. 5 oriented so as to produce a convolution of two input functions.

Assume now that the angle Ⓗ is equal to −45°. This corresponds to positioning the spatial filter in the frequency plane as shown in FIG. 7. Under these conditions, Equation (36) is given by $$t_0'(x_0',y_0') \simeq 2[B_1B_2 + g_1(\sqrt{2} x_0') * g_2(-\sqrt{2} x_0')] \quad (39)$$

Considering for this case the one-dimensional relationship $t_0'(x_0',0)$, then the finite limits on the signal length can be reinserted into this result and $$t'(x',0) = 2[B_1B_2 + g_1(\sqrt{2} x_0') * g_2(-\sqrt{2} x_0')] \text{rect}(x_0'/2R_0) \quad (40)$$

Inasmuch as $g_2$ is a real function, the second term in this equation is the crosscorrelation of $g_1(\sqrt{2} x_0')$ and $g_2(\sqrt{2} x_0')$. The light amplitude distribution along the $x_i'$-axis $(y_i' = 0)$ is directly related to the crosscorrelation of $g_1$ and $g_2$ plus a constant bias term $B_1B_2$.

Thus, by proper orientation of the longer axis of the narrow slit spatial filter, it is possible to optically determine the convolution and crosscorrelation functions for the real one-dimensional signals $g_1$ and $g_2$.

Further, if the two signals $g_1(t)$ and $g_2(t)$ were initially transcribed at different sweep rates, it is still possible to optically convolve and correlate these signals by the appropriate choice of the angle Ⓗ. For example, assume that the signal $g_1(t)$ is transcribed at a writing rate $\alpha$ such that this signal is represented in the spatial domain by $g_1(x/\alpha)$. Also, assume that $g_2(t)$ is transcribed at a different writing rate $\beta$ such that this signal is represented in the spatial domain by $g_2(x/\alpha)$. By choosing the angle Ⓗ of the spatial filter to be $$Ⓗ = \tan^{-1} \alpha/\beta \quad (41)$$

then, if Ⓗ is positive the light amplitude distribution in the image plane along the corresponding $x_i'$-axis is related to the convolution of the two signals. If Ⓗ is negative, the distribution along the corresponding $x_i'$-axis is related to the crosscorrelation of the two signals.

In summary, it is possible by this optical technique to simultaneously process two real one-dimensional signals. By recording the signals on separate density-modulated transparencies and cascading (i.e., superposing) the transparencies in a predetermined orientation in the input plane, then the distribution in the frequency plane contains spectral information about each individual signal and the product of the frequency spectra for these signals. Spatially filtering this distribution using a narrow slit filter appropriately positioned in the frequency plane enables optical determination of the convolution or the correlation function for the two signals.

Returning now to the embodiment of FIG. 3, the circular aperture (6 mm diameter) in element 23 preceding the lens 24 was used to limit the area of the input plane 27 to a circular region of approximately 1.0 cm in diameter, as indicated by reference numeral 27A.

The density modulated transparencies previously described were used as the input signal transparencies and placed in the input plane 27 or as close to it as possible. Single exposure transparencies were separately mounted in conventional 35 mm slide holders. Two such supported transparencies were optically cascaded (juxtaposed) and appropriately positioned in the input plane 27 of the optical system.

The narrow slit spatial filter 38 comprised a pair of double-edged razor blades separated by a distance of 0.26 mm. Each razor blade was sprayed with flat black paint to reduce surface reflections. The spatial filter was symmetrically positioned about the origin of the frequency plane 26 and was oriented along a horizontal axis. The position of the spatial filter was held constant in the frequency plane while the input transparencies were appropriately oriented in the input plane to perform either the convolution or the correlation operation. Thus, instead of rotating the spatial filter to the appropriate position in the frequency plane, the cascaded input transparencies were rotated in the input plane to the proper orientation to perform these operations. The distance, $b$, from the input plane to the frequency plane was 52.4 cm. At this distance and with the radius $R_o$, of the input circular aperture equal to 0.5 cm, the diameter of the central maximum of the Airy pattern was equal to 0.082 mm. Thus, the spatial filter width (W = 0.26 mm) was approximately three times the Airy disk central diameter. For nearly maximum accuracy in computing the convolution and correlation functions, a slit width approximating the Airy disk central diameter is required. However, in practice, using nonprecision positioning equipment, a spatial filter with a slit width dimension slightly greater than ideal is much more easily positioned.

Three similar 52 mm diameter, 193 mm focal length coated achromatic lenses were used in the optical system. The third lens 33 shown in FIG. 3 was used to magnify the distribution, $U_{i_1}(x_{i_1}, y_{i_1})$, in the first image plane 32. The distribution, $U_{i_2}(x_{i_2}, y_{i_2})$, in the second image plane 34 was thus a magnified (by a factor $d_4/d_3$) and a spatially inverted version of the distribution in the first image plane. Since the distribution in the first image plane was a magnified, inverted, spatially filtered version of the input plane distribution, the distribution in the second image plane was a magnified, noninverted spatially filtered version of the input plane distribution. The mathematical descripttion of $U_{i_2}(x_{i_2}, y_{i_2})$ is given by $$U_{i_2}(x_{i_2},y_{i_2}) = \frac{d_1 d_3}{d_2 d_4} \exp\left[\frac{j2\pi}{\lambda}(d_1+d_2+d_3+d_4)\right]$$

$$\exp\left[\frac{j\pi}{\lambda d_4}(1 + \frac{d_3}{d_4})(x_{i_2}^2 + y_{i_2}^2)\right]$$

$$\exp\left[\frac{j\pi}{\lambda D_2}(1 + \frac{d_1}{d_2} - \frac{d_1^2}{bd_2})\right.$$

$$\left.(\frac{d_3^2}{d_4^2})(x_{i_2}^2 + y_{i_2}^2)\right]$$

$$t_o'(\frac{d_1 d_3}{d_2 d_4} x_{i_2}, \frac{d_1 d_3}{d_2 d_4} y_{i_2})$$

where $t_o'$ is the spatially filtered version of the input transmittance function. The distances were:

$d_1 = 74.8$ cm $d_2 = 26.1$ cm $d_3 = 24.4$ cm $d_4 = 96.0$ cm

Thus, the total magnification was $$M = d_2 d_4 / d_1 d_3 = 1.37 \tag{43}$$

Figure 8:
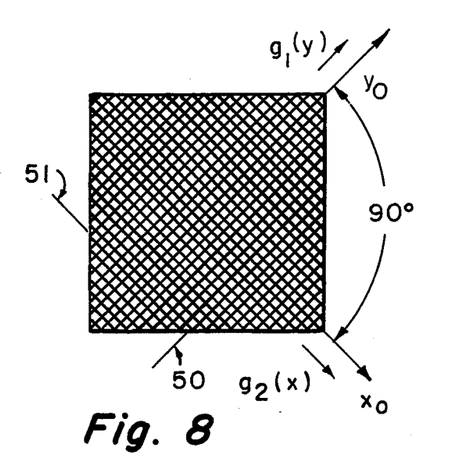
FIGS. 8, 9 and 10 are idealized plots respectively of density-modulated transparencies at the input plane, the resulting optical pattern at the frequency plane; and the resulting optical pattern at the image plane.

Turning now to FIG. 8, reference numeral 50 designates a first intensity-modulated transparency having its one-dimensional information extending along the $x_0$ axis. The function is designated $g_2(x)$. Similarly, a second opaque transparency is designated 51 extending along the $y_0$-axis, and designated $g_1(y)$.

In the illustrated embodiment, the functions $g_1$ and $g_2$ are sine waves, for purposes of illustration, although it will be appreciated that the invention is not limited to any particular mathematical functions. These transparencies are placed of the input plane designated 27 in FIG. 3.

Figure 9:
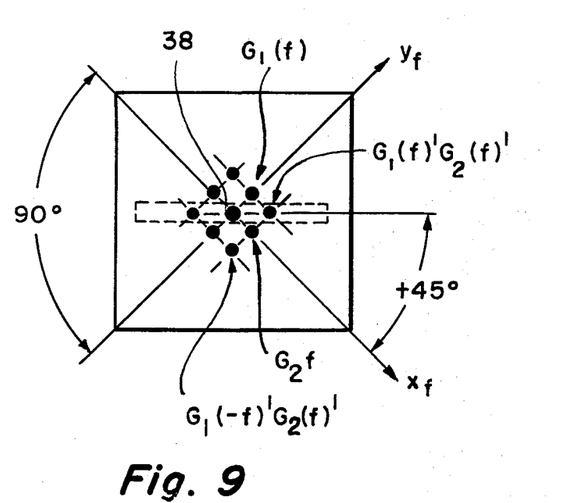

What is seen at the frequency plane 26 is shown in FIG. 9. The pattern illustrated is the first transform (to the frequency plane) of the input functions. At the axis designated $+45°$, the information represents the function $G_1(f)'G_2(f)'$. At the $-45°$-axis, the function is the function $G_1(-f)'G_2(f)'$.

Figure 10:
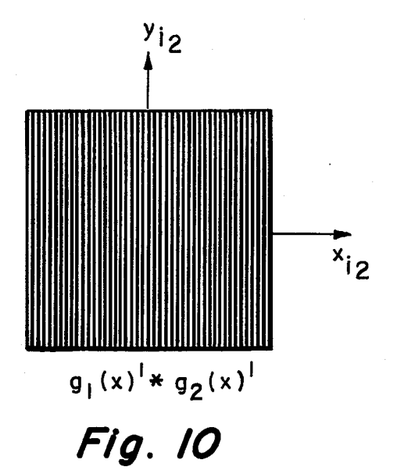

In FIG. 10, there is shown, for the input functions of FIG. 8, the resulting second transform with the slot 38 oriented as indicated in FIG. 9 (to produce the convolution function). This illustration is taken at the second image plane 34 in FIG. 3.

Figure 11:
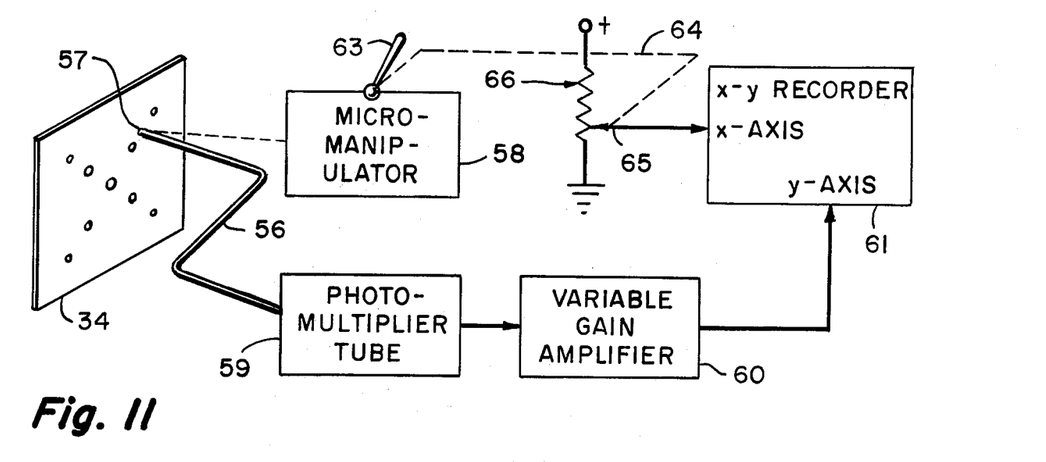
FIG. 11 is a functional block diagram of a system which is used to detect the intensity of the resulting image patterns and record them.

Turning now to FIG. 11, there is shown a system for recording the intensity of the functions which have been described—in the example given, for example, the intensity of the resulting function along the $+45°$ axis at the frequency plane could be recorded, but perhaps more important, the inverse transform at the second image plane along the $x_{i_2}$ axis.

The light pattern at the image plane 34 is transmitted to photomultiplier tube 59 by a fiber optic bundle 56. The input end of the fiber optic bundle is designated 57, and it is positioned by means of a micromanipulator 58 as desired by the operator. The output of photomultiplier tube 59 feeds a variable gain amplifier 60. The output of the variable gain amplifier 60 is a signal which represents the light intensity at the image plane 34 at the position at which the input end 57 of the fiber optic bundle is located. It will be recalled that this light intensity is a square function of the light amplitude, and that the light amplitude is representative of the mathematical function of interest. The output of the variable gain amplifier 60 is connected to the Y-axis drive of an X/Y recorder 61.

The micromanipulator is positioned by means of a handle 63 which is mechanically coupled as at 64 to the wiper arm 65 of a potentiometer 66. One end of the potentiometer 66 is grounded, the the other is supplied with a voltage. Hence, the signal at the wiper arm 65 is representative of the location of the handle 63 of the micromanipulator which, in turn, is representative of the position of the input end 57 of the fiber optic bundle 56. This signal is used to drive the X-axis of the recorder 61. Thus, the recorder 61 produces a record of the light transmittance intensity at the image plane 34 as a function of the position along an axis on the image plane.

In practice, the fiber optic bundle 56 may be a single glass fiber having a diameter of 80 microns, and sealed in a section of opaque electrical wire insulation. One end of the fiber is attached to the micromanipulator. The output end of the fiber optic element is placed in a light-tight box, with the photomultiplier tube, and it is directed toward the photo-emissive surface of the tube. Thus, as the fiber optic element 56 is positioned along the axis desired to be recorded, the light intensity as a function of position was plotted on the X-Y recorder 61.

Figure 12:
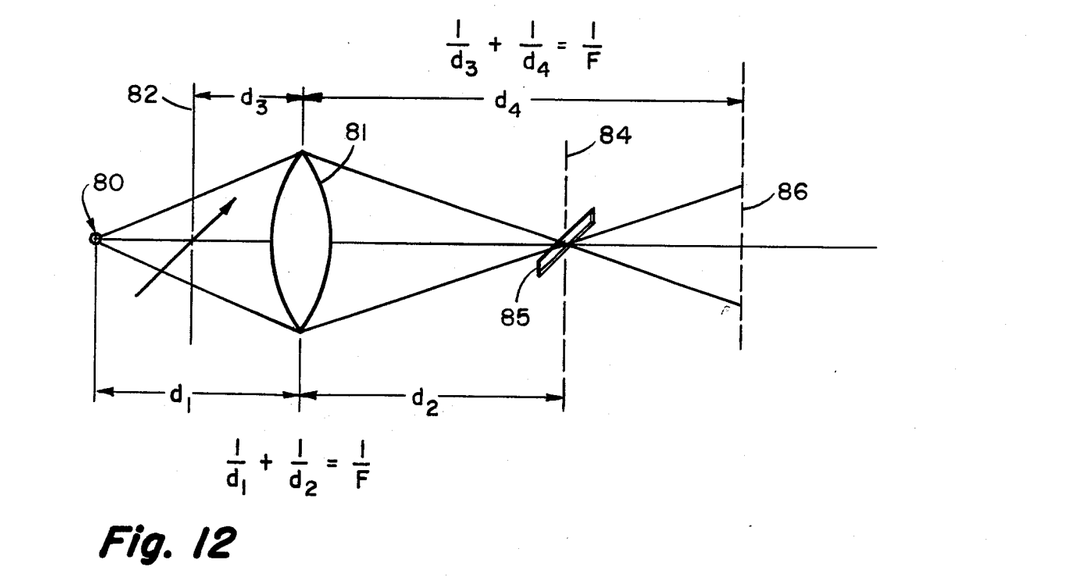
FIG. 12 is a diagrammatic illustration of an alternative optical system for simultaneously processing two density-modulated transparencies.

In the embodiment of FIG. 3, the lenses 31, 33 form a compound lens for adjusting the mangification of the resulting image. It will thus be appreciated that three separate lenses are used in this embodiment. In the embodiment of FIG. 4, only two lenses are shown. Turning now to FIG. 12, an embodiment is shown wherein only a single lens is used for performing both transforms. In this embodiment, reference numeral 80 generally designates a point source of light, and 81 is a single covering lens having a focal length F.

The input plane is designated 82, and it will be seen to be located between the point source 80 and the lens 81. In other words, the intensity-modulated transparencies are located in the plane 82, and they may be prepared in the manner disclosed above. The point source 80 is imaged in a frequency plane 84, and, again, a slit 85 is located in the frequency plane 84. The transparencies are focused on a first image plane 86. The distances of the frequency plane and first image plane are determined as indicted in the drawing.

The advantage of this embodiment, as indicated, is that only a single lens is used to perform both transforms. Further, by using fewer optical elements, there are fewer alignment problems in setting up the system.

With the present invention, the inherent two-dimensional parallel processing capabilities of a relatively simple optical system enable simultaneous, real-time spectral analysis of two appropriately cascaded density modulated signal transparencies representing real one-dimensional inputs. It has been shown that these spectral descriptions of two independent inputs are simultaneously available along the $f_x$- and $f_y$-axes of the frequency plane. Furthermost, the off-axis distribution contains spectral information which can be used to determine the convolution and correlation relationships between the input functions.

For real input functions, the off-axis distribution along the $+45°$ diagonal in the frequency plane is seen to be the product of the common spectra of the inputs, the Fourier transform of which is the folded convolution function for such real inputs. These frequency domain components can be utilized for such a computation by simply placing a narrow slit spatial filter along the $+45°$ diagonal in the frequency plane and inverse transforming through the use of a second lens system.

The off-axis distribution along the $-45°$ diagonal in the frequency plane contains the product of the frequency spectrum of one input function and the folded spectrum of the second input function. For real input functions, the Fourier transform of this distribution is the correlation function relating the input transparencies. As in the case of convolution, a narrow slit filter oriented along the $-45°$ diagonal permits the second lens system to transform only these off-axis components of interest.

In contrast to one prior art technique for convolution and correlation, this method does not require the laborious production of a holographic frequency plane filter. This constitutes a significant advantage when one-dimensional data records are to be analyzed.

Having thus disclosed a number of embodiments of the invention, persons skilled in the art will be able to substitute equivalent elements for those illustrated and to modify certain of the procedures that have been disclosed while continuing to practice the principle of the invention, and it is, therefore, intended that all such modifications and substitutions be covered as they are embraced within the spirit and scope of the appended claims.

We claim:

1. An optical processing system comprising:
   light source means for transmitting monochromatic light along a predetermined path;
   first lens means for focusing said light from said source onto said path at a location defining a frequency plane;
   first and second image means each bearing a density-modulated input optical pattern extending along one dimension parallel to an information axis and located in juxtaposed relation in said light path at an input plane, said information axes of said first and second image means being in predetermined relation at an angle greater than zero in a plane transverse of said light path, whereby the product of the Fourier transforms of said optical signals on said image means is directly formed at said frequency plane;
   spatial filter means in said path at said frequency plane for permitting passage of only a selected portion of incident light; and
   second lens means for focusing light in said path passing through said spatial filter means onto an image plane such that the image on said image plane defines the product of the Fourier transforms of the frequency spectra of said input optical signals.

2. The system of claim 1 wherein said input plane is located between said first lens means and said frequency plane.

3. The system of claim 1 wherein said spatial filter means comprises a narrow slit filter having a direction of elongation assuming a predetermined orientation in the frequency plane.

4. The system of claim 1 wherein said first and second image means each comprise a transparency having a light amplitude transmission along an information axis which is representative of the amplitude of the corresponding input signal to be processed.

5. The system of claim 4 wherein said information axes of said first and second image means are oriented at 90° relative to each other.

6. The system of claim 5 wherein said spatial filter means comprises a narrow slit filter having a direction of elongation oriented at a predetermined angle relative to the orientation of the informationn axes of said first and second image means.

7. The system of claim 6 wherein the direction of elongation of said narrow slit is $+45°$ relative to a horizontal axis defined by the information axis of one of said image means, thereby to yield a convolution between said input signals.

8. The system of claim 6 wherein said slit is oriented at a $-45°$ angle relative to a horizontal axis defined by the information axis of one of said image means, thereby to define a correlation function of the two input signals.

9. The system of claim 1 wherein said second lens means comprises a pair of lenses to adjust the magnification of the resulting optical image at said image plane.

10. An optical processing system comprising light source means for transmitting monochromatic light along a predetermined path; means for focusing said light from said source onto said path at a location defining a frequency plane; first and second image means each bearing a density-modulated input optical signal extending along an information axis and located in juxtaposed relation at an input plane in said light path between said source means and said focusing means, said information axes of said first and second image means defining a predetermined angular relation greater than zero degrees; spatial filter means in said light path at said frequency plane for permitting passage of only a selected portion of incident light; thereby to directly generate the product of the Fourier transforms of the frequency spectra of said input optical signals at an image plane spaced along said path from said frequency plane.

11. The system of claim 10 wherein said spatial filter means comprises a thin, elongated slit extending at a predetermined angle relative to the information axes of said first and second image means.

12. The system of claim 10 further comprising detection means for detecting the optical intensity of said combined frequency spectra in said image plane and for generating an electrical signal representative thereof; and means for recording said signal representative of intensity as a function of position in said image plane.

13. A method of simultaneously processing first and second input signals comprising: optically recording said signals respectively on first and second transparencies such that the light amplitude transmission of each transparency is representative of the associated input signal along an information axis, placing said first and second transparencies in juxtaposed position with their respective information axes at an angle greater than zero at an input plane; illuminating said transparencies with a converging beam of monochromatic light focused on a frequency plane to directly form an image representative of the product of the Fourier transforms of the frequency spectra of the optical records on said first and second transparencies at said frequency plane; spatially filtering said light on said frequency plane along a predetermined axis transverse of said path; and focusing the light passing through said spatial filter onto an image plane such that one of the convolution and correlation of said input signals appears on said image plane.

14. The method of claim 13 wherein the light amplitude transmission of each transparency parallel to an information axis is proportional to the amplitude of the associated input signal.

15. The method of claim 13 further comprising the step of detecting the optical signal of said combined frequency spectra in said image plane.

* * * * *